United States Patent [19]

Leichnitz

[11] Patent Number: 5,092,183
[45] Date of Patent: Mar. 3, 1992

[54] DEVICE FOR COOLING TESTING TUBES
[75] Inventor: Kurt Leichnitz, Gross Grönau, Fed. Rep. of Germany
[73] Assignee: Drägerwerk Aktiengesellschaft, Lübeck, Fed. Rep. of Germany
[21] Appl. No.: 491,333
[22] Filed: Mar. 9, 1990
[30] Foreign Application Priority Data
Mar. 14, 1989 [DE] Fed. Rep. of Germany ....... 3908195
[51] Int. Cl.5 ...................... G01N 1/22; G01N 31/22; F25D 7/00
[52] U.S. Cl. .................. 73/863.11; 422/83; 422/88; 62/109
[58] Field of Search ........... 73/863.11, 863.12, 864.71, 73/864.73, 864.74, 864.34, 864.35; 62/62, 109, 316, 64, 373; 422/83-89

[56] References Cited
U.S. PATENT DOCUMENTS

Re. 33,567  4/1991  Killip et al. ............ 73/863.11
3,133,444   5/1964  Karwat .................. 73/863.12
3,196,689   7/1965  Forrester et al. ........ 73/863.11
3,357,256  12/1967  Burch ................... 73/863.11
3,919,065  11/1975  Heden ................... 62/56 X

FOREIGN PATENT DOCUMENTS 1934028  1/1971  Fed. Rep. of Germany ... 73/863.11
 203934 12/1982  Japan .................... 73/863.12
2129933  5/1984  United Kingdom .......... 73/863.11

Primary Examiner—Tom Noland
Attorney, Agent, or Firm—McGlew & Tuttle

[57] ABSTRACT

The present invention pertains to a device for cooling testing tubes during sampling by evaporating a liquid. The cooling device causes a controlled cooling effect that is practically independent of the state of the ambient air during the sampling and is easy to handle. After flowing through the testing tube (2), the gas to be investigated flows through a layer of filler (7) that surrounds the testing tube (2) and is impregnated with a liquid.

5 Claims, 1 Drawing Sheet

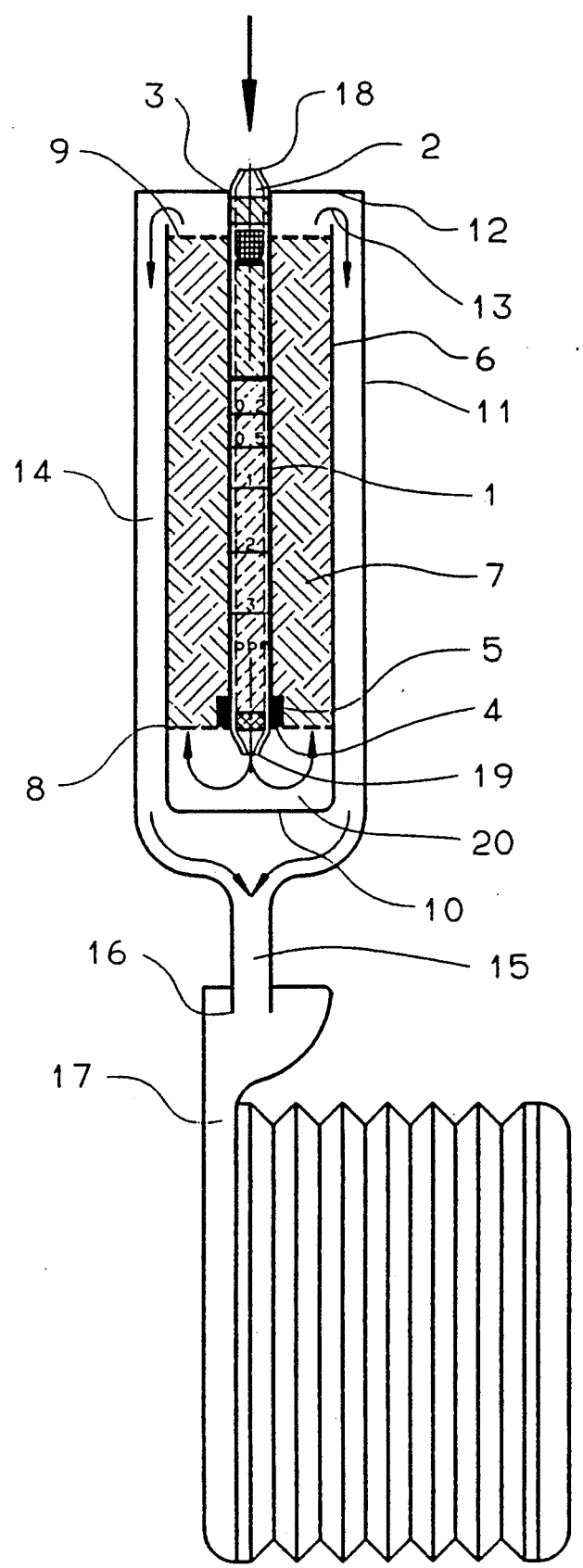

5,092,183

DEVICE FOR COOLING TESTING TUBES

FIELD AND BACKGROUND OF THE INVENTION

The present invention pertains to a device for cooling testing tubes by evaporating a liquid during sampling.

Testing tubes are widely used in conjunction with a appropriate pump for measuring gases, vapors, and aerosols in air and industrial gases. Due to the properties of the reagent systems used in the testing tubes, measurements are possible, in general, only at temperatures of up to a maximum of about 40° C. Unpredictable changes in the indication behavior of the testing tubes may occur above this temperature limit because of the evaporation of reagents.

It is possible to investigate gases with temperatures above 40° C. if the gas and/or the testing tube is cooled. The common practice is to place a probe in front of the testing tube and to wrap both the probe and the testing tube with a few layers of plastic foam. The plastic foam is kept moist during the measurement. The probe (and consequently also the gas to be investigated) are cooled due to the extraction of heat of vaporization (K. Leichnitz: Prüfrohrchen-Messtechnik [Test Tube Measurement Technology], Ecomed-Verlagsgesellschaft mbH, 1981).

One disadvantage of this process is the uncontrolled cooling effect, which strongly depends on the temperature, the humidity, and the state of movement of the ambient air. In addition, handling of the wet plastic foam is very complicated, and errors made during wrapping and moistening influence the cooling effect.

SUMMARY AND OBJECTS OF THE INVENTION

It is an object of the present invention to provide a cooling device for testing tubes, which brings about a controlled cooling effect that is practically independent of the state of the ambient air during sampling and is easy to handle.

This task is accomplished by passing the gas to be investigated—after it flows through the testing tube—through a layer of filler material impregnated with a liquid, which layer envelopes the testing tube.

The advantage of the present invention is the fact that the cooling effect begins in a controlled manner during the sampling, regardless of the state of the ambient air. Another advantage is the fact that hardly any cooling liquid is lost during the pauses between the measurements. Frequent re-moistening of the cooling device therefore becomes unnecessary. The loss of cooling liquid can be reduced even further by closing the two openings of the cooling device with stoppers during prolonged intervals between measurements. The design of the cooling device permits simple, and clean handling, without coming into contact with the cooling liquid.

The filler, which is used to absorb the cooling liquid and to bring it into contact with the gas flow, over a large surface area, is preferably a granular, porous material, such as silica gel, aluminum oxide, or an aluminum silicate. However, it is also possible, in principle, to use any absorbent material that is permeable to air, e.g., felt or plastic foam.

A highly volatile substance, such as ether or an alcohol, is preferably used as the cooling liquid. Water can also be used as the cooling liquid. The cooling liquid selected substantially determines the intensity o the cooling effect.

A particularly easy-to-handle, compact, and efficiently operating cooling device is realized by using three tubes nested in one another and extending axially into one another. The inner tube is used to receive the testing tube, the middle tube contains the filler, and between the middle and outer tubes, the air sample, being delivered successively through testing tubes and filler, is drawn off into the delivery member, e.g., a bellows type pump.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only figure is a schematic diagram showing a preferred embodiment of the invention.

DETAILED DESCRIPTION OF THE PREFERRED EMBODIMENT

The cooling device consists essentially of three tubes placed concentrically one in another. The inner tube 1 is used to receive the testing tube 2. A rubber ring 5 is placed on the end 4 of tube 1 opposite the testing tube insertion end 3. This rubber ring 5 is used to seal the testing tube 2 against the tube 1 and to fix the testing tube 2.

A middle tube 6 is arranged substantially concentric with the inner tube 1. The radius of the middle tube 6 is larger than that of the inner tube 1 by about 10 mm. The annular gap formed between the tubes 6 and 1 is filled with a loose packing 7 of silica gel granules. The perforated disks 8, 9 fix the loose packing in the annular gap in the axial direction without hindering the gas flow through the loose packing.

At its end opposite the testing tube insertion end 3, the middle tube 6 is closed gas-tight with a plate 10.

At its end, the outer tube 11, whose radius is about 4 mm larger than that of the middle tube, is connected gas-tight by the disk 12 to the testing tube insertion end 3 of the inner tube 1. The middle tube 6 ends about 4 mm in front of the disk 12, so that a gas canal 13 is left open. The annular gap between the middle tube 6 and the outer tube 11 also forms a gas canal 14.

At its end opposite testing tube insertion end 3, the outer tube 11 tapers to the diameter of a testing tube. This tapered end forms the connection piece 15, which is inserted into the receiving opening 16 of a pump 17 instead of a testing tube.

To bring the cooling device into a ready-to-operate state, the filler 7 must be impregnated with the cooling liquid. To do so, the cooling device is held vertically with the testing tub insertion end 3 pointing upward. A small amount of cooling liquid is subsequently poured into the inner tube 1; it will collect on said plate 10. The cooling liquid is subsequently tilted into the horizontal position and at the same time rotated through at least 360° about its longitudinal axis. This causes the cooling liquid to flow into the filler. The cooling liquid will be distributed uniformly due to capillary forces.

If the cooling device is to be stored in this ready-to-operate state for a rather long time, the two openings (3, 15) are closed by closing stoppers (not shown). The cooling agent is thus prevented from evaporating prematurely.

To put the cooling device into operation, a testing tube 2, which is open at both ends, is pushed into the inner tube 1 until it is held by the seal 5. The cooling device with its connection piece 15 is subsequently inserted into the receiving opening 16 of the pump 17.

After being put into operation, the pump 17 draws the gas to be investigated in through one end 18 of said testing tube 2. It flows out through the other end 19; the gas enters into chamber 20, and flows through the filler. Intense evaporation of the cooling agent begins here due to the movement of the gas and the elevated temperature of the gas. The heat of vaporization removed leads to cooling of the filler 7 of the inner tube 1 and ultimately of the testing tube 2. This makes it possible to maintain the temperature of the testing tube below the limit value of 40° C, even if the gas being drawn in has a temperature exceeding 100° C.

The gas flowing through the filler 7 passes through the gas canal 14 and the connection piece 15 and into the pump 17. The cooling agent is condensed here sooner or later.

However, since venting of the pump after each measurement is also required by the specifications, the cooling agent is removed from the pump during the venting.

After the measurement, the testing tube 2 is removed from the cooling device and can be read. After inserting a new testing tube, the next measurement can be started immediately.

While a specific embodiment of the invention has been shown and described in detail to illustrate the application of the principles of the invention, it will be understood that the invention may be embodied otherwise without departing from such principles.

What is claimed is :

1. Device for cooling testing tubes during sampling, comprising: filler means, enveloping the test tube, said filler means being impregnated with liquid; and, gas passage means for passing gas to be investigated through the test tube and subsequently through the layer of filler for cooling the gas upon evaporation of said liquid.

2. A device according to claim 1, wherein said filler includes a granular, porous material selected from the group consisting of silica gel, aluminum oxide, and aluminum silicate.

3. A device according to claim 1, wherein said liquid is a volatilizing substance.

4. A device according to claim 3, wherein said volatilizing substance is selected from the group consisting of ether and alcohol.

5. A device according to claim 1, wherein said passage means includes an inner tube used for receiving the testing tube, a middle tube and a outer tube, said filler material being arranged between said inner tube and said middle tube, a gas canal being defined between said middle tube and said outer tube, said inner tube being connected gas-tight at a first end faced adjacent a testing tube insertion end, said inner tube being in fluid communication with said middle tube at an end opposite the testing tube insertion end, said middle tube having a gas-tight closure opposite said testing tube insertion end., an end of the outer tube opposite the testing tube insertion end having a taper leading into a connection piece, said connection piece for connection to a sampling device.

* * * * *